United States Patent
Falsini et al.

(10) Patent No.: US 6,733,490 B1
(45) Date of Patent: May 11, 2004

(54) METHOD AND APPARATUS FOR CONTROLLING SUB-CLINICAL LASER PROCEDURES WITH INTRA-OPERATIVE MONITORING OF ELECTROPHYSIOLOGICAL CHANGES

(75) Inventors: Benedetto Falsini, Rome (IT); Giorgio Dorin, Cupertino, CA (US)

(73) Assignee: Iridex Corporation, Mountain View, CA (US)

( * ) Notice: Subject to any disclaimer, the term of this patent is extended or adjusted under 35 U.S.C. 154(b) by 0 days.

(21) Appl. No.: 10/121,951

(22) Filed: Apr. 12, 2002

Related U.S. Application Data

(60) Provisional application No. 60/283,540, filed on Apr. 12, 2001.

(51) Int. Cl.$^7$ ................................................. A61F 9/007
(52) U.S. Cl. .............................. 606/4; 606/10; 606/13; 607/88; 128/898
(58) Field of Search .............................. 128/898; 606/3, 606/4, 10–13; 607/88, 89

(56) References Cited

U.S. PATENT DOCUMENTS 5,297,554 A * 3/1994 Glynn et al. ................. 351/206
6,540,391 B2 * 4/2003 Lanzetta et al. ............ 362/276

* cited by examiner

Primary Examiner—David M. Shay
(74) Attorney, Agent, or Firm—Paul Davis; Heller Ehrman White & McAuliffe

(57) ABSTRACT

A method of monitoring and controlling the sub-threshold laser treatment of a patient's retina. Sensors are located on a patient to measure focal electroretinograms (FERG). A stimulating beam is delivered onto the patient's retina. A pre-treatment FERG signal is collected. Treatment FERG signals are collected while treating the retina with a sub-threshold laser treatment. A difference is determined between the pre-treatment and treatment FERG signals. The difference is used to control the termination of the treatment.

56 Claims, 2 Drawing Sheets

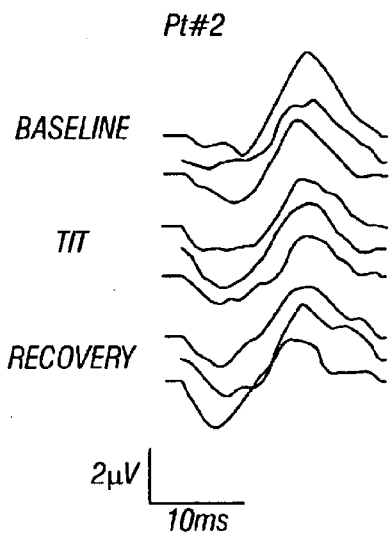
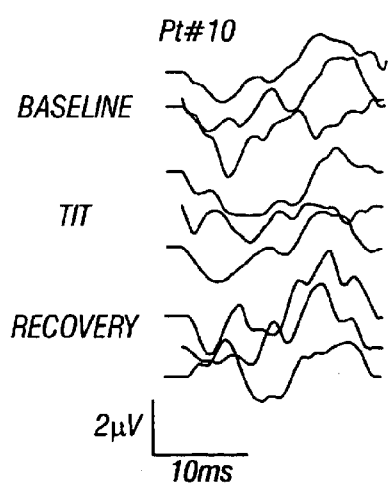
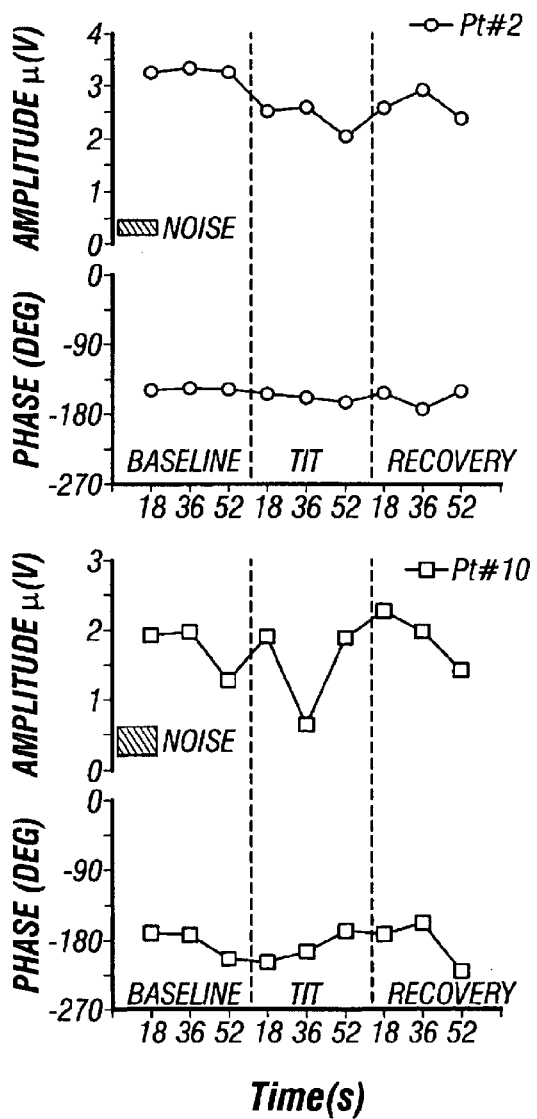
FIG. 2A  FIG. 2B

METHOD AND APPARATUS FOR CONTROLLING SUB-CLINICAL LASER PROCEDURES WITH INTRA-OPERATIVE MONITORING OF ELECTROPHYSIOLOGICAL CHANGES

CROSS-REFERENCE TO RELATED APPLICATIONS

This application claims the benefit of priority from U.S. Provisional Patent Application Ser. No. 60/283,540 filed Apr. 12, 2001, which is incorporated herein by reference in its entirety.

BACKGROUND

1. Field of the Invention

This invention relates to an apparatus and method for performing minimally invasive ocular laser treatments, and more particularly to an ophthalmic laser device configured for activating localized photothermal and/or photochemical processes while affected electrophysiological functions are maintained without exceeding pre-settable thresholds of change.

2. Description of the Related Art

There are several pathologies of the eye that cause some form of visual impairment up to and including blindness. A number of pathologies are currently treated with lasers such as glaucoma and retinal disorders. Retinal disorders treatable with laser include diabetic retinopathy, macular edema, central serous retinopathy and age-related macular degeneration (AMD).

Diabetic retinopathy represents the major cause of severe vision loss (SVL) for people up to 65 years of age, while AMD represents the major cause of SVL in people over 65 years of age. More than 32,000 Americans are blinded from diabetic retinopathy alone, with an estimated 300,000 diabetics at risk of becoming blind. The incidence of AMD in the USA is currently estimated at 2 million new cases per year, of which 1.8 million are with the "dry" form and 200,000 are with the "wet" form, also defined as choroidal neovascularization (CNV). CNV causes subretinal hemorrhage, exudates and fibrosis, any of which can lead to SVL and legal blindness.

A widely used form of laser treatment for retinal disorders is called laser photocoagulation (P.C.). Laser P.C. has become the standard treatment for a number of retinal disorders such as diabetic retinopathy, macular edema, central serous retinopathy, retinal vein occlusion and CNV. Laser P.C. is a photo-thermal process, in which heat is produced by the absorption of laser energy by targeted tissues, for the purpose of inducing a thermal "therapeutic damage", which causes biological reactions and, ultimately, beneficial effects. Conventional retinal P.C. relies on some visible "blanching" of the retina as the treatment endpoint and can be defined as Ophthalmoscopically Visible Endpoint Photocoagulation (or OVEP) treatment. Since the retina is substantially transparent to most wavelengths used in laser P.C., its "blanching" is not caused directly by the laser. Visible "blanching" is the sign that the normal transparency of the retina has been thermally damaged by the conduction of heat generated underneath the retina in laser absorbing chromophores (i.e. melanin) contained in the retinal pigment epithelium (RPE) and in choroidal melanocytes.

The thermal gradient or elevation can be controlled by the laser (i) irradiance (power density), (ii) exposure time and/or (iii) wavelength. High thermal elevations are normally created with current OVEP clinical protocols that aim to produce visible endpoints ranging from intense retinal whitening (full thickness retinal burn) to barely visible retinal changes. Using the endpoint of visible retinal blanching is a practical way to assess the laser treatment, but it also constitutes disadvantageous and unnecessary retinal damage, which in turn results in a number of undesirable adverse complications including some vision loss, decreased contrast sensitivity and reduced visual fields in a substantial number of patients.

The damage of intense laser burns may also trigger neovascularization, a serious and highly undesirable event leading to further loss of vision. Due to the drawback of iatrogenic visual impairment due to thermal damage to the neurosensory retina, conventional OVEP laser treatment is presently considered and administered only late in the course of the disease, when it has become "clinically significant" and the benefit-to-risk ratio justifies the risk of associated negative effects. Recent clinical studies have suggested that patients with certain types of disorders could benefit from earlier treatment.

Various lasers procedures, referred to as minimum intensity photocoagulation (MIP), are now pursuing the beneficial therapeutic effects with invisible very light treatments with the goals to minimize iatrogenic retinal damage and to maximize the preservation of retinal tissue and visual functions. Less damaging MIP could be administered earlier in the course of the disease to patients with less compromised vision and with overall better results. For example, MIP is now experimentally administered to patients diagnosed with "dry" AMD presenting with high-risk drusen, as a prophylactic treatment to prevent or delay SVL due to the progression toward the "wet" neovascular stage. Another such example is transpupillary thermotherapy (TTT) (Reichel et al., 99) for the treatment of subfoveal occult CNV, a condition previously left untreated until it progresses into the visually devastating classic CNV.

All these treatments avoid visible retinal laser burns and can be defined as Non Ophthalmoscopically Visible Endpoint Photocoagulation or NOVEP treatment, to differentiate from the conventional OVEP treatment. Unfortunately, the absence of a visible endpoint during the laser treatment makes it difficult to select the proper irradiation dosage for each individual patient and leaves the physician with no tangible sign of having achieved the proper threshold for the minimum therapeutic damage (MTD). To make these treatments more popular and consistent, there is a need for a device and a method that allows intra-operative monitoring of sub-clinical changes during the laser treatment, able to provide the doctor with information about the treatment's effects and/or to control and terminate the laser emission at a given pre-settable threshold of functional change. This would significantly decrease the difficulty associated with NOVEP procedures and would favor the acceptance by the ophthalmic community.

Recording of intra-operative electro-retinal functional changes can be performed using ElectroRetinoGram, Focal ElectroRetinoGram, or Multi-Focal ElectroRetinoGram. All of these are retinal evoked potential signals and will be referred to, collectively, as FERG. FERG can be spontaneous or elicited by flickering light stimulation and non-invasively detected and recorded through skin electrodes. The FERG has proven to be a sensitive indicator of macular cone system dysfunction in different retinal degenerative diseases (Seiple et al., 1986; Falsini et al., 1996), including age-related macular degeneration (Sandberg et al., 1993; Falsini et al., 1998). The FERG signals generated by flicker stimulation can be recorded and evaluated in terms of reliability and statistical robustness by steady-state, frequency-domain analysis techniques (Porciatti et al., 1989; Falsini et al., 2000). In addition, real-time retrieval and analysis of the responses to a set of stimulus parameters (sweep techniques) can be employed in a clinical setting to evaluate macular dysfunction (Seiple et al., 1993; Falsini et al., 2000).

To gather information from FERG signals a discrete Fourier analysis (Fadda et al., 1989) is performed on the average signal of multiple FERG responses to isolate the FERG fundamental harmonic. Amplitude (in microvolts) and phase (in degrees) can then be determined. Standard errors of the amplitude and phase estimates, derived from the block averages, are then calculated to determine response reliability. Averaging and Fourier analysis is also performed on signals sampled asynchronously from the temporal frequency of the stimulus, to derive an estimate of the background noise at the fundamental component. These FERG signals could be used to determine changes to the overlying neurosensory retina by monitoring the signal responses before treatment at a baseline level and then during treatment. Changes in electrophysiological signals would indicate changes to the patient's retina caused by laser treatment.

The acceptance and adoption of NOVEP treatments by the ophthalmic community could be facilitated and accelerated if new user-friendly laser devices were available to allow the safe and consistent administration of NOVEP treatments. MIP treatment protocols would potentially be administered early in the course of the disease with better outcomes and would become the new standard-of-care. It is proposed by this patent that a method and apparatus utilizing intra-operative monitoring of electro-physiological changes would allow a laser surgeon to more easily perform NOVEP treatments. Accordingly, there is a need for FERG recorded through the use of electrodes in order to provide the real time monitoring of intra-operative electrophysiological functional changes from baseline.

SUMMARY OF THE INVENTION

Accordingly, an object of the present invention is to provide a system, and its method of use, that uses FERG recorded through the use of electrodes in order to provide the real time monitoring of intra-operative electrophysiological functional changes from baseline.

Another object of the present invention is to provide a system, and its method of use, for performing clinically effective NOVEP laser treatment with the minimum possible thermal damage to the overlying neurosensory retina by monitoring FERG signals before, during, and after treatment.

These and other objects of the present invention are achieved in a method of monitoring and controlling the sub-threshold laser treatment of a patient's retina. Sensors are located on a patient to measure focal electroretinograms (FERG). A stimulating beam is delivered onto the patient's retina. A pre-treatment FERG signal is collected. Treatment FERG signals are collected while treating the retina with a sub-threshold laser treatment. A difference is determined between the baseline and treatment FERG signals. The difference is used to control the termination of the treatment.

In another embodiment of the present invention, a method of monitoring and controlling the sub-threshold laser treatment of a retina locates electrode sensors on a patient to measure FERGs. A stimulating beam is delivered onto the patient's retina. A pre-treatment FERG signal is collected. Treatment FERG signals are collected while treating the retina with a sub-threshold laser treatment. A difference is between the pre-treatment and treatment FERG signals. The difference is used by a physician to control a termination of the treatment.

In another embodiment of the present invention, a system for monitoring and controlling the sub-threshold laser treatment of a patient's retina includes at least two sensors to measure FERGs. A laser delivery system includes a laser treatment beam, an aiming beam, and a stimulating beam, each co-aligned onto the retina. Resources convert the FERG signal changes into parameters to control the laser for an optimum sub-threshold treatment.

BRIEF DESCRIPTION OF THE DRAWINGS

FIGS. 2(a) and 2(b) are graphical illustrations that show representative FERGs before treatment (baseline), during treatment (TTT) and after treatment (recovery).

DETAILED DESCRIPTION OF THE PREFERRED EMBODIMENTS

Figure 1:
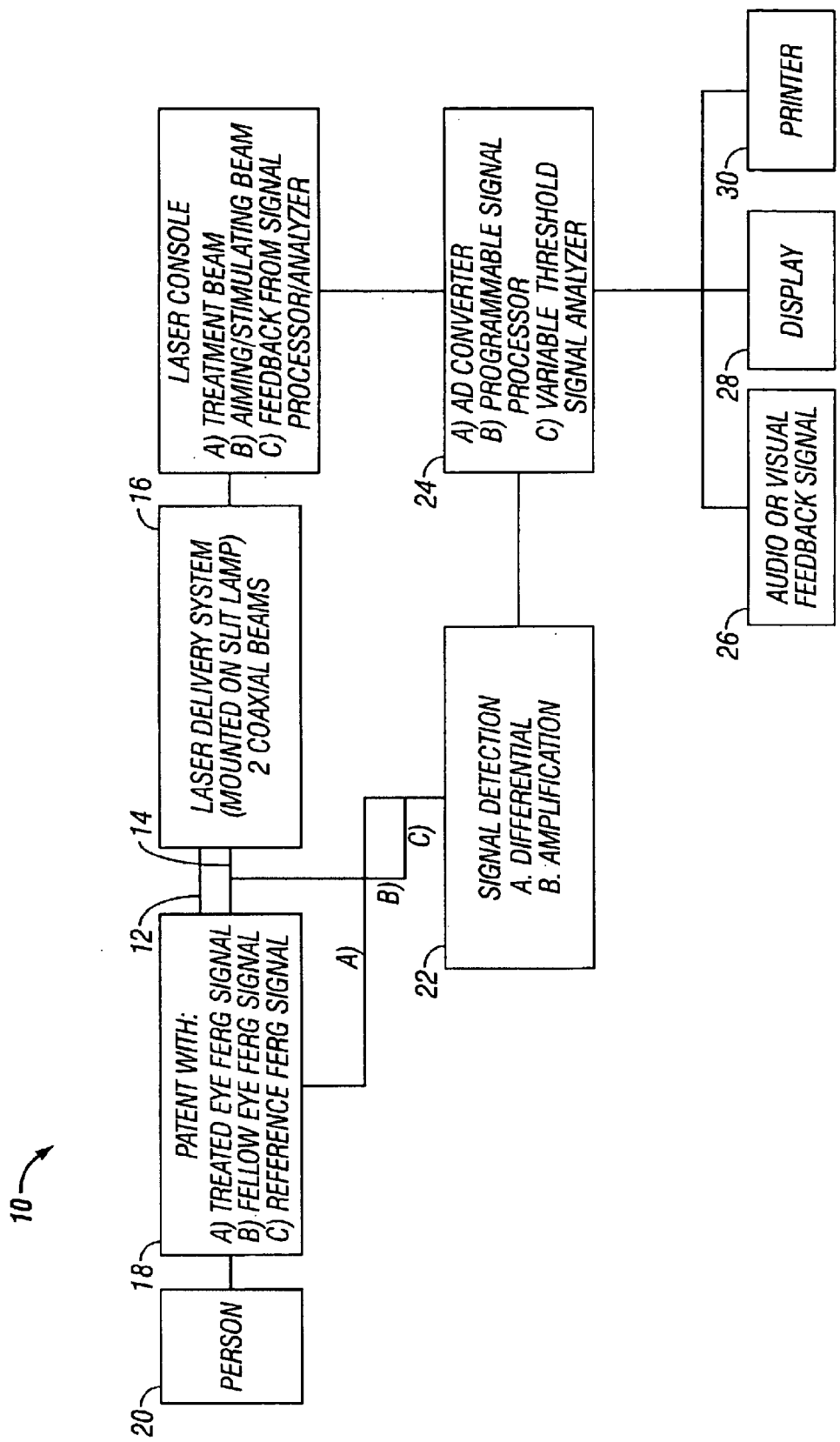
FIG. 1 is a schematic block diagram of one embodiment of the present invention that illustrates a system for monitoring and controlling the sub-threshold laser treatment of a patient's retina.

In various embodiments, the present invention provides systems, and their method of use, for performing minimally invasive ocular laser treatments under real time monitoring and control of treatments that have sub-clinical (invisible) effects through the change of evoked electro-retinal potentials. In one embodiment, the present invention provides ophthalmic laser devices, and their methods of use, that are configured for activating localized photothermal and photochemical processes while affected electrophysiological functions are maintained without exceeding pre-settable thresholds of change. In one specific embodiment, an ophthalmic laser device of the present invention is configured to activate localized photothermal and photochemical processes while affected electrophysiological functions are monitored to prevent exceeding pre-settable thresholds of change.

In another embodiment, the present invention provides a device for performing minimally invasive laser treatments that are capable of inducing beneficial therapeutic effects through laser induced sub-clinical effects. These sub-clinical effects are not ophthalmoscopically visible to the surgeon but can be revealed by the change of electrophysiological functions detectable during the treatment through FERG signals. FERG signal changes from baseline can be used for manual or automatic intra-operative control of the laser irradiation.

As illustrated in FIG. 1, one embodiment of a system 10 for monitoring and controlling the sub-threshold laser treatment of a patient's retina provides a treatment beam 12 and an aiming beam 14 from a laser delivery system 16 that are delivered to one eye of a patient 18. Suitable treatment laser delivery systems 16 include but are not limited to argon, dye, Nd:YAG, Nd:Vanadate, Alexandrite, Krypton, and the like. The system of the present invention is configured to administer sub-visible-threshold treatments while providing a flickering FERG stimulus and a FERG feedback signal proportional to the actual level of sub-clinical thermal damage. This signal can be used (i) as a perceptible (acoustic or visible) signal to guide the physician to the treatment endpoint, or (ii) employed for the automatic control of the intensity and the duration of the laser delivery system 16 emission.

Aiming beam 14 is combined with treatment beam 12 by laser delivery system 16 to be coaxial so that they are delivered to the exact same spot on the retina of patient 18. The FERG stimulus is developed by adapting aiming beam 14 of laser delivery system 16 and consists of a spot of flickering light. By way of illustration, and without limitation, the flickering light can have a frequency from 5 to 120 Hz. Further, the flickering light can be generated by an LED. By way of illustration, and without limitation, the LED can have a peak wavelength of 630 nm and a mean luminance of approx 100 cd/m2), square-wave modulated at 41 Hz (modulation depth approx. 90%, 50% duty cycle). Other suitable aiming beam sources include but are not limited to, red LEDs, red laser diodes, tungsten with red filters, and generally any visible light source, which can be seen by the physician while wearing laser treatment glasses (which usually stop green and/or blue light).

Aiming beam 14 need not be the same as the excitation or stimulation flicker. Aiming beam 14 can be any visible wavelength provided that it is collinear with the treatment beam 12, and the flicker source can be any visible wavelength at all, including simple white light. Aiming beam 14, irrespective of wavelength, can be used as a flicker source. Further, aiming beam 14 can be delivered and viewed through any ocular lens, including but not limited to a standard Goldmann-type lens in Maxwellian view. It will be appreciated that other delivery and viewing lenses can also be utilized.

In various embodiments, a stimulus field size of treatment beam 12 can be from 10 to 30 degrees in diameter and centered on a fovea by visual inspection. A large, for example 60 degrees, light adapting background can be kept at the same mean luminance as the stimulus and utilized to minimize stray-light.

In one embodiment, FERG recording, acquisition and analysis is performed by electrodes 20 differential amplifiers 22, and computer programs 24. Retinal signals can be recorded with any sensors, including but not limited to disposable non-corneal electrodes and/or electrodes integrated onto corneal contact lenses. A first electrode 20 monitors the signal from the treatment eye. A second electrode 20 monitors the signal from the normal untreated eye. A third electrode 20 monitors a reference signal. In one specific embodiment, the reference signal is on the forehead between the eyes. The differential signal (treated eye signal minus the untreated eye signal) is then amplified 22, filtered 22 and digitized 24.

FIGS. 2(*a*) and 2(*b*) illustrates examples of FERGS signals generated by two different patients who were treated with a TTT protocol of the present invention. Signal amplitude and phase values are recorded at the different experimental times, with an average temporal resolution of 18-sec. Noise amplitude is represented by a rectangular box displayed in the amplitude plot indicating the minimum-maximum range. FERG amplitude decreased from baseline values during TTT in both patients and recovered to pre-treatment values over 60 sec when TTT was stopped. As illustrated, patients 2 and 10 had the largest and smallest recorded signal-to-noise ratios, respectively.

Blocks of events with various numbers of individual FERG responses are averaged 24 with rejection of single sweeps exceeding a threshold voltage in order to minimize noise coming from blinks or eye movements. A discrete Fourier analysis 24 can be performed in order to isolate the FERG fundamental harmonic, whose amplitude, in microvolts, and phase, in degrees, are determined.

Before treatment, a "baseline" FERG is recorded. Response amplitude and phase data for all measurements are calculated and the data can be stored on disk for further off-line analysis and/or for patient records.

The laser treatment is then started. During treatment, FERG signals are recorded ("TTT" FERG). Individual blocks of the treatment FERG are statistically compared to the baseline FERG. Relative amplitude and phase changes are analyzed and correlated to the total estimated amount of hyperthermia delivered during the treatment. These signals are used as feedback to the physician by audible, visual and other like indictors 26, and output the progress and status of treatment. Alternatively, the feedback can be used to control the treatment parameters to drive the treatment to a successful completion automatically.

After the treatment, FERG signals are recorded ("Recovery" FERGs). The Recovery FERGs are compared to the baseline or pre-treatment FERGS to confirm that there was no permanent change, or damage, to the retina. The Recovery FERGs can be stored on disk, paper 30, and the like, for further off-line analysis and/or for patient records.

Intra-operative FERG monitoring (treatment FERG) is used to assess non-invasively functional damage to neurosensory retina during treatment and offers a quantitative approach to determine an optimal laser dose protocol. The methods and systems of the present invention minimize functional damage to the retina by indicating current treatment status to the user by audio/visual feedback 26, a display 28 and/or a printed display 30 (FIG. 1). Later analysis of the relationship between FERG changes and treatment parameters will help to understand and optimize how local hyperthermia acts in vivo on the function of degenerated AMD retinas. This helps the refinement and optimization of the clinical application of the laser treatment technique.

Furthermore, the real-time FERG monitoring methods and systems of the present invention can be used to control the intensity and duration of laser delivery during treatment applications. The characteristics, including but not limited to amplitude and/or phase of the electrical responses derived from FERG changes during the treatment exposure are recorded in real-time from the neurosensory retina, and can provide the input variables to generate a real-time feedback signal that is proportional to the amount of induced change.

The feedback signal, filtered through adjustable thresholds, can be made available in various ways (i.e. as an acoustic tone, with an optical display, a head's up display, as well as any audio or visible indicator, in a slit lamp delivery system) to guide the physician during the sub-visible-threshold treatment to ensure that the appropriate level of hyperthermia is delivered to each patient. An acceptable level of the FERG signal can be defined and the laser will automatically turn off if the signal goes beyond this threshold level. The same feedback signal can be optionally used for the automatic control of the intensity of the laser emission to maintain a certain threshold signal while the treating physician controls the length of the treatment (total dosage). Alternatively, the feedback signal can automatically end the treatment once the desired dosage is reached, while maintaining the laser emission within the same (or different) intensity threshold as above.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art.

What is claimed is:

1. A system for monitoring and controlling the sub-threshold laser treatment of a patient's retina, comprising:
   at least two sensors to measure focal electroretinograms (FERG);
   a laser delivery system including a laser treatment beam, an aiming beam, and a stimulating beam, each co-aligned onto the retina; and
   first resources to convert the FERG signals into an indicator for the physician.

2. The system of claim 1, wherein the first resources include electronics, a digital converter, a computer and an algorithm.

3. The system of claim 1, wherein the second resources include a computer and algorithm.

4. The system of claim 1, wherein the sensors are electrodes.

5. The system of claim 1, wherein the difference is utilized to minimize thermal damage to the overlying neurosensory retina undergoing treatment.

6. The system of claim 1, further comprising:
   collecting recovery FERG signals after treatment of the retina.

7. The system of claim 1, wherein the sub-threshold treatment minimizes the occurrence of blanching of the retina that is treated.

8. The system of claim 1, wherein the sub-threshold treatment minimizes the occurrence of laser burns to healthy retinal tissue.

9. The system of claim 1, wherein the sub-threshold treatment minimizes the occurrence of neovascularization.

10. The system of claim 1, wherein the difference is used to establish a therapeutic window of treatment for a variety of ocular conditions and disorders.

11. The system of claim 1, wherein the sub-threshold treatment provides a minimum threshold of therapeutic effectiveness of treatment and is below a threshold that creates irreversible damage to the retina.

12. The system of claim 1, wherein a first sensor is positioned on a reference eye surface, and a second sensor is positioned on a treatment eye surface.

13. The system of claim 12, wherein each of the first and second sensors is directly coupled to the reference and treatment eye surfaces respectively.

14. The system of claim 1, wherein each of the first and second sensors is positioned on a template.

15. The system of claim 14, wherein the template is a bandage contact lens.

16. A system for monitoring and controlling the sub-threshold laser treatment of a patient's retina, comprising:
   at least two sensors to measure focal electroretinograms (FERG);
   a laser delivery system including a laser treatment beam, an aiming beam, and a stimulating beam, each co-aligned onto the retina;
   first resources to convert the FERG signals into a parameter to control a laser treatment; and
   second resources to control the laser treatment for an optimum sub-threshold treatment.

17. The system of claim 16, wherein the first resources include electronics, a digital converter, a computer and an algorithm.

18. The system of claim 16, wherein the second resources include a computer and algorithm.

19. The system of claim 16, wherein the sensors are electrodes.

20. The system of claim 16, wherein the difference is utilized to minimize thermal damage to the overlying neurosensory retina undergoing treatment.

21. The system of claim 16, further comprising:
   collecting treatment FERG signals after treatment of the retina.

22. The system of claim 16, wherein the sub-threshold treatment minimizes the occurrence of blanching of the retina that is treated.

23. The system of claim 16, wherein the sub-threshold treatment minimizes the occurrence of laser burns to healthy retinal tissue.

24. The system of claim 16, wherein the sub-threshold treatment minimizes the occurrence of neovascularization.

25. The system of claim 16, wherein the difference is used to establish a therapeutic window of treatment for a variety of ocular conditions and disorders.

26. The system of claim 16, wherein the sub-threshold treatment provides a minimum threshold of therapeutic effectiveness of treatment and is below a threshold that creates irreversible damage to the retina.

27. The system of claim 16, wherein a first sensor is positioned on a reference eye surface, and a second sensor is positioned on a treatment eye surface.

28. The system of claim 27, wherein each of the first and second sensors is directly coupled to the reference and treatment eye surfaces respectively.

29. The system of claim 16, wherein each of the first and second sensors is positioned on a template.

30. The system of claim 29, wherein the template is a bandage contact lens.

31. A method of monitoring and controlling the sub-threshold laser treatment of a patient's retina, comprising:
   locating sensors on a patient to measure focal electroretinograms (FERG);
   delivering a stimulating beam onto the patient's retina;
   collecting a pre-treatment FERG signal;
   collecting treatment FERG signals while treating the retina with a sub-threshold laser treatment;
   determining a difference between the pre-treatment and treatment FERG signals; and
   using the difference to control the termination of the treatment.

32. The method of claim 31, wherein the sensors are electrodes.

33. The method of claim 31, wherein the difference is utilized to minimize thermal damage to the overlying neurosensory retina undergoing treatment.

34. The method of claim 31, further comprising:
   collecting recovery FERG signals after treatment of the retina.

35. The method of claim 31, wherein the sub-threshold treatment minimizes the occurrence of blanching of the retina that is treated.

36. The method of claim 31, wherein the sub-threshold treatment minimizes the occurrence of laser burns to healthy retinal tissue.

37. The method of claim 31, wherein the sub-threshold treatment minimizes the occurrence of neovascularization.

38. The method of claim 31, wherein the difference is used to establish a therapeutic window of treatment for a variety of ocular conditions and disorders.

39. The method of claim 31, wherein the sub-threshold treatment provides a minimum threshold of therapeutic effectiveness of treatment and is below a threshold that creates irreversible damage to the retina.

40. The method of claim 31, wherein a first sensor is positioned on a reference eye surface, and a second sensor is positioned on a treatment eye surface.

41. The method of claim 40, wherein each of the first and second sensors is directly coupled to the reference and treatment eye surfaces respectively.

42. The method of claim 31, wherein each of the first and second sensors is positioned on a template.

43. The method of claim 42, wherein the template is a bandage contact lens.

44. A method of monitoring and controlling the sub-threshold laser treatment of a retina, comprising:

locating electrode sensors on a patient to measure FERGs;

delivering a stimulating beam onto the patient's retina;

collecting a pre-treatment FERG signal;

collecting treatment FERG signals while treating the retina with a sub-threshold laser treatment;

determining a difference between the pre-treatment and treatment FERG signals; and providing the difference to a physician to control a termination of the treatment.

45. The method of claim 44, wherein the sensors are electrodes.

46. The method of claim 44, wherein the difference is utilized to minimize thermal damage to the overlying neurosensory retina undergoing treatment.

47. The method of claim 44, further comprising:

collecting treatment FERG signals after treatment of the retina.

48. The method of claim 44, wherein the sub-threshold treatment minimizes the occurrence of blanching of the retina that is treated.

49. The method of claim 44, wherein the sub-threshold treatment minimizes the occurrence of laser burns to healthy retinal tissue.

50. The method of claim 44, wherein the sub-threshold treatment minimizes the occurrence of neovascularization.

51. The method of claim 44, wherein the difference is used to establish a therapeutic window of treatment for a variety of ocular conditions and disorders.

52. The method of claim 44, wherein the sub-threshold treatment provides a minimum threshold of therapeutic effectiveness of treatment and is below a threshold that creates irreversible damage to the retina.

53. The method of claim 44, wherein a first sensor is positioned on a reference eye surface, and a second sensor is positioned on a treatment eye surface.

54. The method of claim 53, wherein each of the first and second sensors is directly coupled to the reference and treatment eye surfaces respectively.

55. The method of claim 44, wherein each of the first and second sensors is positioned on a template.

56. The method of claim 55, wherein the template is a bandage contact lens.

* * * * *